(12) United States Patent
Berr et al.

(10) Patent No.: US 11,213,264 B2
(45) Date of Patent: Jan. 4, 2022

(54) POSITRON EMISSION TOMOGRAPHY SYSTEMS AND METHODS

(71) Applicant: University of Virginia Patent Foundation, Charlottesville, VA (US)

(72) Inventors: Stuart S. Berr, Crozet, VA (US); Stanislaw Majewski, Morgantown, WV (US); JosE Maria Benlloch Baviera, Valencia (ES); Antonio Javier Gonzalez Martinez, Valencia (ES)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/778,053

(22) PCT Filed: Nov. 23, 2016

(86) PCT No.: PCT/US2016/063534
§ 371 (c)(1),
(2) Date: May 22, 2018

(87) PCT Pub. No.: WO2017/091697
PCT Pub. Date: Jun. 1, 2017

(65) Prior Publication Data
US 2018/0344274 A1 Dec. 6, 2018

Related U.S. Application Data

(60) Provisional application No. 62/258,861, filed on Nov. 23, 2015.

(51) Int. Cl.
*G01T 1/20* (2006.01)
*A61B 6/00* (2006.01)
(Continued)

(52) U.S. Cl.
CPC .......... *A61B 6/4488* (2013.01); *A61B 5/0035* (2013.01); *A61B 6/037* (2013.01);
(Continued)

(58) Field of Classification Search
CPC ... A61B 6/4488; A61B 5/0035; A61B 6/4417; A61B 6/037; G01R 33/481; G01F 1/66
See application file for complete search history.

(56) References Cited

U.S. PATENT DOCUMENTS

| 4,584,478 A | 4/1986 | Genna et al. |
| 4,677,299 A * | 6/1987 | Wong .................... G01T 1/1644 |
| | | 250/363.03 |

(Continued)

FOREIGN PATENT DOCUMENTS

JP  2000346948 A  * 12/2000

OTHER PUBLICATIONS

International Search Report and Written Opinion dated Apr. 4, 2017, in International Application No. PCT/US2016/063534 (10pgs.).

*Primary Examiner* — Kiho Kim
(74) *Attorney, Agent, or Firm* — Finnegan, Henderson, Farabow, Garrett & Dunner LLP (57) ABSTRACT

A positron emission tomography (PET) assembly includes an annular housing and an annular scintillator disposed within the annular housing. The annular scintillator includes an annular, substantially continuous crystal scintillator tube configured to absorb ionizing radiation and to emit light energy. A plurality of photo detectors are annularly disposed around the annular scintillator within the annular housing and configured to detect the emitted light energy.

18 Claims, 5 Drawing Sheets

(51) Int. Cl.
*G01F 1/66* (2006.01)
*A61B 6/03* (2006.01)
*G01R 33/48* (2006.01)
*A61B 5/00* (2006.01)

(52) U.S. Cl.
CPC .............. *A61B 6/4417* (2013.01); *G01F 1/66* (2013.01); *G01R 33/481* (2013.01)

(56) References Cited

U.S. PATENT DOCUMENTS

| | | | | |
|---|---|---|---|---|
| 4,755,680 | A * | 7/1988 | Logan | G01T 1/1642 |
| | | | | 250/363.01 |
| 5,338,937 | A | 8/1994 | Daghighian et al. | |
| 7,310,407 | B2 * | 12/2007 | Juni | G01T 1/1611 |
| | | | | 250/363.05 |
| 9,599,722 | B2 * | 3/2017 | Laurence | G01T 1/1644 |
| 2004/0004188 | A1 * | 1/2004 | Tai | G01T 1/2985 |
| | | | | 250/363.03 |
| 2005/0023473 | A1 * | 2/2005 | Burr | G01T 1/1611 |
| | | | | 250/368 |
| 2006/0243913 | A1 * | 11/2006 | Overdick | G01T 1/2008 |
| | | | | 250/361 R |
| 2011/0301918 | A1 | 12/2011 | Haselman et al. | |
| 2014/0084170 | A1 | 3/2014 | Wieczorek et al. | |
| 2014/0361181 | A1 | 12/2014 | Liu | |
| 2016/0312117 | A1 * | 10/2016 | Wieczorek | G01T 1/2985 |
| 2016/0367205 | A1 * | 12/2016 | Galbiati | A61B 6/037 |

* cited by examiner

POSITRON EMISSION TOMOGRAPHY SYSTEMS AND METHODS

CROSS-REFERENCE TO RELATED APPLICATIONS

This application is a U.S. national phase entry of International Application No. PCT/US2016/063534, filed Nov. 23, 2016, which claims the benefit of priority based on U.S. Provisional Patent Application No. 62/258,861, filed Nov. 23, 2015, to both of which this application claims the benefit of priority, and the entirety of the subject matter of both of which is incorporated herein by reference.

TECHNICAL FIELD

The disclosure relates generally to positron emission tomography (PET) imaging systems and, more particularly, to PET devices for use alone or in multi-modality imaging systems.

BACKGROUND

Imaging instrumentation has improved dramatically over the past couple of decades. Magnetic resonance imaging (MRI) is one modality that provides a wide amount of data, as compared to other imaging techniques. MRI can be used to create images with excellent soft tissue signal and contrast. MRI can also be used to measure motion and flow, metabolites (MR spectroscopy), diffusion of water, temperature, etc. However, compared to other imaging modalities, it is comparatively insensitive as a molecular imaging modality. One modality that is better than MRI for detecting and quantifying exceedingly small amounts of exogenously administered material is positron emission tomography (PET).

Some prior systems have combined MRI and PET imaging together by using serially acquired images on different scanners. However, with such systems, the acquired images have a time delay, during which the patient or the patient's anatomy may shift, introducing imaging errors. Additionally, the spatial resolution of such systems may be lower than desirable for certain applications. Accordingly, a need exists for PET systems that address one or more of these drawbacks.

SUMMARY

In one embodiment, the PET scanner is based on a single tube made of a scintillator crystal. This feature may eliminate the need for multiple smaller crystals, and effectively remove all edges from the detector. This may also remove the edge distortions and improve the spatial resolution of the detector, as compared to multiple crystal systems. In addition, because there are no gaps between detector elements and between rings of detectors in some embodiments, the sensitivity of the scanner may increase.

In one embodiment, the PET scanner is based on a scintillator tube that includes multiple smaller elements that are joined together to form a pseudo single crystal tube. This embodiment may enable building larger PET scanners based on the edge-less crystal tube design for use in pediatric or adult human scanners.

In one embodiment, a multi-modality imaging system includes a frame having an outer transaxial wall and an inner transaxial wall, the inner wall defining a transaxially extending bore configured to receive a patient. For use in conjunction with a MRI scanner, the inner transaxial space may be occupied by a radiofrequency (RF) coil. The system further includes a positron emission tomography (PET) assembly including an annular scintillator disposed between the inner transaxial wall and the outer transaxial wall. The annular scintillator may include an annular, substantially continuous crystal scintillator tube.

In another embodiment, a positron emission tomography (PET) assembly includes an annular housing and an annular scintillator disposed within the annular housing. The annular scintillator may include an annular (e.g., tubular), substantially continuous crystal scintillator configured to absorb ionizing radiation and to emit light energy. A plurality of photodetectors are annularly disposed around the annular scintillator within the annular housing and configured to detect the emitted light energy.

In another embodiment, a multi-modality imaging system includes a frame having an outer transaxial wall and an inner transaxial wall defining an axially extending bore configured to receive a patient. A radio frequency (RF) coil is disposed within the inner transaxial wall and the outer transaxial wall and configured to generate radio frequency energy to image the patient. A positron emission tomography (PET) assembly includes an annular scintillator disposed between the inner transaxial wall and the outer transaxial wall about the RF coil. The annular scintillator includes an annular, continuous crystal scintillator tube. A plurality of photomultipliers are disposed on the outer surface of the annular scintillator farther from the transaxially extending bore than an inner surface of the annular scintillator.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

As discussed in further detail below, various embodiments of a positron emission tomography (PET) assembly are provided. The PET assembly may be configured for use in a standalone PET system or in combination with other imaging modalities, such as magnetic resonance imaging (MRI) and/or X-ray based imaging (e.g., computed tomography (CT)). In some embodiments, the PET assembly may include an annular scintillator having an annular (e.g., tubular), substantially continuous crystal scintillator configured to convert ionizing radiation into light energy detectable by one or more photodetectors. In some implementations, the foregoing feature may enable the PET system utilizing the PET assembly to have improved spatial resolution, as compared to multi-crystal systems.

Further, in some embodiments, by providing a substantially continuous, annular (e.g., tubular) crystal scintillator and containing the light such to avoid light spread throughout the crystal, a PET device having high spatial-resolution close to the spatial resolution theoretically limited by positron range may be achieved. Additionally, this spatial resolution may be maintained throughout the field of view of the device, as opposed to some conventional systems that experience reduced spatial resolution in certain areas of the field of view. Further, embodiments of the PET systems described herein may have high sensitivity, good energy and timing resolution, and the ability to handle high count rates, as compared to conventional systems including multiple or discontinuous crystal scintillators.

Figure 1:
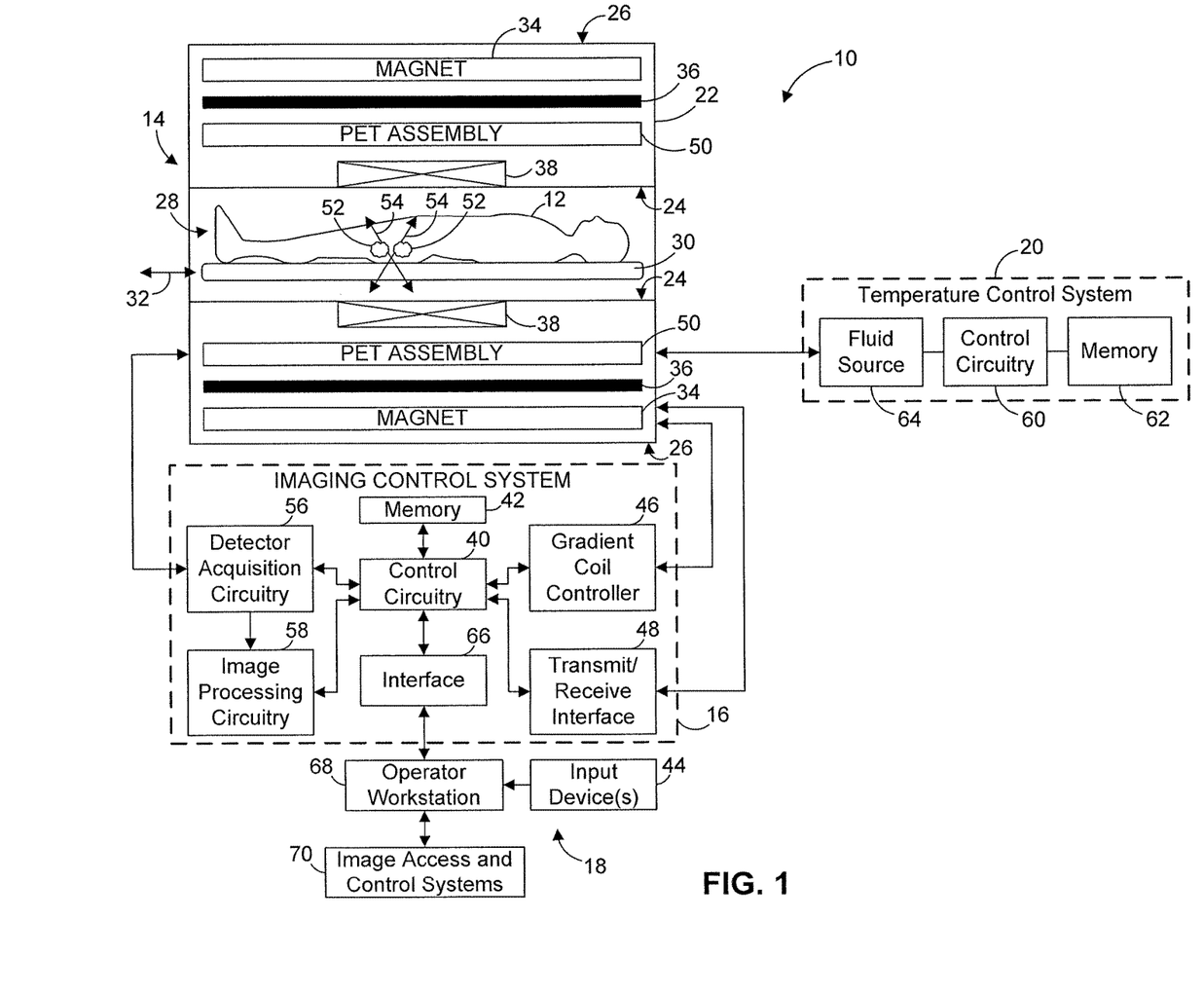
FIG. 1 illustrates an embodiment of a multi-modality imaging system having a PET assembly.

Turning now to the drawings, FIG. 1 diagrammatically illustrates an imaging system 10 for imaging a patient 12. However, the depiction of a patient is merely an example. The patient 12 may be any target object, any, human, and so forth, in other embodiments. The imaging system 10 includes an imaging device 14, an imaging control system 16, a health care facility system 18, and a temperature control system 20. During operation, the imaging device 14 is configured to image the patient 12 via one or more imaging modalities under control of the control system 16. The control system 16 may receive one or more inputs from the health care facility system 18 regarding operation of the device and output data related to imaging of the patient 12. The temperature control system 20 may coordinate with the control system 16 to facilitate cooling of one or more components of the imaging device 14 during operation.

In the illustrated embodiment, the imaging device 14 includes a frame 22 having an inner transaxial wall 24 and an outer transaxial wall 26. The inner transaxial wall 24 may define a transaxially extending bore 28 configured to receive a patient support 30. The patient support 30 may be configured to position the patient 12 within the transaxially extending bore 28, for example, via movement of the patient support 30 within, or into and out of, the frame 22, as indicated by arrow 32.

In the illustrated embodiment, the imaging system 10 is a combined PET and MRI imaging system. However, it should be noted that in other embodiments, the imaging system 10 may combine PET with any other suitable imaging modality, such as X-ray CT or ultrasound. Indeed, the depicted MRI/PET system is merely an example.

In the depicted embodiment, the imaging device 14 includes components suitable for performing both MRI and PET. Specifically, the MRI portion of the device 14 may include a magnet 34 configured to generate a primary magnetic field. In some embodiments, the magnet 34 may be driven by a power source (not shown) provided, for example, by control system 16. One or more gradient coils 36 may be configured to generate magnetic gradient fields during imaging. A radio frequency (RF) coil 38 may generate RF pulses for exciting the nuclear spins and/or function as a receiving coil, depending on the given implementation. The arrangement of the magnet 34, the one or more gradient coils 36, and the RF coil 38 is subject to a variety of implementation-specific variations. However, in the illustrated example, the RF coil 38 is nested within the one or more gradient coils 36, which are nested within the magnet 34.

Centralized control circuitry 40 may control both the MRI and PET subsystems of the imaging system 10. With respect to the MRI sub-system, the control circuitry 40 may control the MRI components to generate a desired magnetic field and RF pulses and to process the generated signals. To that end, the control circuitry 40 may include one or more processors communicatively coupled to memory 42. The one or more processors (e.g., microprocessor(s), application-specific integrated circuit (ASIC), field-programmable gate array (FPGA), etc.) may be configured to execute a control algorithm. By way of example, the control algorithm may be provided as machine-readable encoded instructions stored on a machine-readable medium, such as the memory 42, and may provide control signals for controlling operation of the imaging system 10. The control signals may control the imaging device 14 to selectively acquire MRI and/or PET data.

The memory 42 may be a tangible, non-transitory, machine readable medium. For example, the memory 42 may be volatile or non-volatile memory, such as read only memory (ROM), random access memory (RAM), magnetic storage memory, optical storage memory, or a combination thereof. Furthermore, a variety of control parameters may be stored in the memory 42 along with code configured to provide a specific output (e.g., enable MRI image acquisition, enable PET image acquisition, etc.) to the imaging device 14 during operation. The memory 42 may also store acquired image data, pulse sequences for different modes of operation, or any other parameters defining examination sequences performed by the MRI portion of the device 14. Further, in some embodiments, the processor(s) of the control circuitry 40 may also receive one or more inputs from one or more input devices 44, through which the user may choose a process and/or input desired parameters (e.g., which part of the body should be imaged, whether multiple or single modality operation is desired, etc.).

In some embodiments, a gradient coil controller 46 and a transmit/receive interface 48 may provide interfaces through which the control circuitry 40 may control the one or more gradient coils 36 and RF coil 38. For example, the gradient coil controller 46 may include amplification circuitry configured to drive current for the one or more gradient coils 36 under control of circuitry 40. For further example, the transmit/receive interface 48 may include amplification circuitry to drive the RF coil 38 during operation. In some embodiments, the RF coil 38 may be configured to both emit RF excitation pulses and receive responsive signals, and the transmit/receive interface 48 may include a switch configured to toggle the RF coil 38 between transmit and receive modes of operation.

In addition to the MRI subsystem, the imaging device 14 also includes one or more components that enable PET imaging. For example, a PET assembly 50 is disposed between the inner transaxial wall 24 and the outer transaxial wall 26 of the frame 22 of the imaging device 14. In the illustrated embodiment, the PET assembly 50 is disposed annularly between the one or more gradient coils 36 and the RF coil 38. However, in other embodiments, the PET assembly 50 may be disposed in any other desired location within the frame 22.

Further, although the PET assembly 50 is illustrated as an integrative part of the frame 22 in the illustrated example, the PET assembly 50 may be configured as a removable insert in other embodiments. For example, the PET assembly 50 may be provided as part of a retrofit kit configured to retrofit an existing imaging system (e.g., MRI system or CT system) to endow the existing system with PET imaging capabilities. Such a retrofit kit may include the PET assembly 50 configured to be inserted into an existing frame 22 and/or software configured to be executed by the control circuitry 40 to enable control of the PET assembly and/or processing of the acquired data.

The PET assembly 50 may include an annular scintillation crystal coupled to one or more photodetectors, as discussed in more detail below, to enable the PET assembly 50 to function as a PET detector. To that end, the patient 12 may be administered a positron-emitting source 52 which will result in the production of a pair of gammas. In some embodiments, the PET subsystem may generate images illustrating the distributions of positron-emitting nuclides in the patient 12. To that end, the PET assembly 50 may operate on the principle of annihilation coincidence detection (ACD). In such embodiments, a positron is emitted by a nuclear transformation of a radiopharmaceutical (e.g., radiation source 52), and the positron annihilates with an electron to result in photons 54 emitted in opposite directions and detected by PET assembly 50. The single crystal scintillator in the PET assembly 50 may detect the photons 54 and produce visible photons detectable by photodetectors.

Detector acquisition circuitry 56 may be configured to control acquisition of the signals acquired by the PET assembly 50 in coordination with central control circuitry 40. Image processing circuitry 58 may process the acquired data from the detector acquisition circuitry 56. For example, the image processing circuitry 58 may include one or more processors configured to receive the PET image data and the MRI image data, and to overlay the PET data over the MRI data to generate a composite image.

In the illustrated embodiment, the centralized control circuitry 40 controls the PET and MRI subsystems of the imaging system 10. To that end, the control of the subsystems is coordinated to enable acquisition of PET and MRI data while the patient 12 is in the same position. The foregoing feature may offer the advantage of enabling reduction in imaging acquisition time (e.g., because the patient does not have to be moved between imaging modalities) and/or reduction in image artifacts due to patient movement.

In some embodiments, the temperature control system 20 may also be under control of the control circuitry 40 to enable cooling of one or more components of the imaging device 14. For example, the temperature control system 20 may include control circuitry 60 (e.g., one or more processors) communicatively coupled to control circuitry 40. The control circuitry 60 may access memory 62 (which may include components similar to memory 42 described above) to facilitate control of a fluid source. For example, the control circuitry 60 may control a pump to pump fluid from the fluid source 64 to one or more tubes in the PET assembly 50 to cool one or more components in the PET assembly 50, as described in more detail below.

Further, the imaging control system 16 may include one or more devices that facilitate interaction between a user and the imaging device 14. For example, an interface 66 may communicatively couple the control circuitry 40 to an operator workstation 68. The operator workstation 68 may be a general purpose or special computer including, for example, memory for storing pulse sequences, examination protocols, patient data, raw and/or processed image data, and so forth.

The operator workstation 68 may receive one or more operator inputs via the user input devices 44. The user input devices 44 may include, but are not limited to, mobile devices (e.g., smartphones, tablets, laptops, etc.), keyboards, computer mice, etc. The operator workstation 68 may also be coupled to one or more local or remote image access and control systems 70, such as picture archiving and communication systems (PACS), teleradiography systems (TELERAD), etc.

Figure 2:
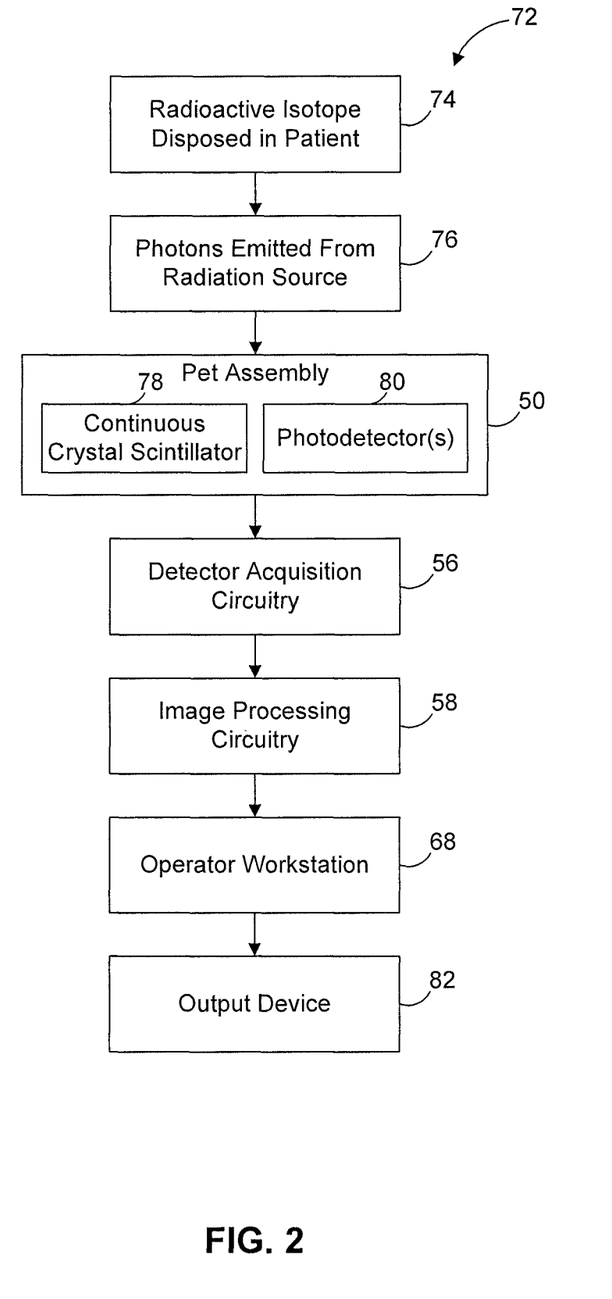
FIG. 2 illustrates an embodiment of a PET system having a continuous crystal scintillator tube.

FIG. 2 illustrates an embodiment of a standalone PET imaging system 72 in accordance with a disclosed embodiment. That is, in this embodiment, the PET assembly 50 may form an integral or removably insertable part of a single modality system 72. As shown, in this embodiment, a radioactive isotope (e.g., radiation source 52) is disposed in the patient 12 (block 74). In some embodiments, the radioactive isotope may be targeted to a desired location(s) within the patient 12 by chemically binding it to a targeting ligand, such glucose, a peptide, small molecule, etc. Photons are emitted from the radioactive isotope 52 (block 76) and detected by one or more detection elements of the PET assembly 50.

In the illustrated embodiment, the PET assembly 50 includes a substantially continuous scintillator crystal 78. The substantially continuous crystal 78 may be formed in a variety of suitable shapes, such as curved or annular. For example, the substantially continuous crystal 78 may be provided as a tube in some embodiments. The substantially continuous crystal scintillator 78 may include only a single crystal. For example, the substantially continuous crystal scintillator 78 may not be pixelated (i.e., the crystal does not include multiple crystals having gaps or crystal edges there between). The substantially continuous crystal scintillator tube may be continuous in composition such that no discontinuities occur throughout its volume.

PET scanners including the continuous crystal scintillator may offer advantages over PET scanners based on numerous, discrete scintillator elements (e.g., cut into smaller elements (pixels) or remaining uncut (continuous)). Presently disclosed embodiments may overcome problems associated with these types of PET scanners that include multiple crystals elements. For example, presently disclosed embodiments may reduce or eliminate the limitations arising from difficulties in the ability to localize where the high energy gamma ray hits due to the edges of every detector element. By reducing the number of elements, a proportional reduction in the resulting localization artifacts may be achieved. This may enable an increase in the overall spatial resolution of the PET scanner.

In one embodiment, the substantially continuous crystal scintillator 78 may include a plurality of crystals held together by an optical matching glue (e.g., Cargille Meltmount™). In this embodiment, the optical matching glue may have a refractive index approximately equal to the refractive index of the crystals such that light propagates through the edges of the crystals into the optical matching glue without refracting. Thus, in some embodiments, the substantially continuous crystal scintillator 78 may have a continuous refractive index throughout its volume even though it includes more than one crystal. That is, in some embodiments, the substantially continuous crystal scintillator 78 may include multiple smaller elements that are joined together to form a pseudo single crystal tube. This embodiment may enable building larger PET scanners based on the edge-less crystal tube design, for example, for use in pediatric or adult human scanners. As used herein, the term "substantially continuous crystal" refers to both continuous crystals and pseudo single crystals.

The substantially continuous crystal scintillator 78 may be formed via any suitable method. For example, in one embodiment, the substantially continuous crystal scintillator 78 may be made by boring through a boule, sized for the given implementation and then polishing the resulting surfaces. In some embodiments, the material used to make the boule may be tested to meet a minimum threshold value for light output. Any inhomogeneities in light output may be measured, and normalization/efficiency factors may be applied during the calibration of the PET assembly 50.

In another embodiment, a plurality of crystals may be glued together with optical matching glue to form a pseudo single crystal embodiment of the substantially continuous crystal scintillator 78, as discussed above. In another embodiment, the crystal could be grown to the desired shape and size needed for the desired imaging application.

One of ordinary skill in the art may expect the properties of the substantially continuous crystal scintillator 78 to result in light spread through the volume of the scintillator due to reflection of the light. However, the present inventors have recognized that the light can be contained to avoid spreading through the scintillator volume. Thus, the inventors have recognized that any expected problems with many overlapping detection events (i.e., pileups) and limited spatial position definition of the initial annihilation photon's conversion point in the scintillator are not experienced to a greater degree than multi-crystal designs. Thus, the present inventors have recognized that the substantially continuous crystal scintillator 78 may enable a practical PET system for both preclinical and clinical imaging.

The proposed scanner may remove all scintillator crystal edges from the active volume. This may improve the homogeneity of the scanner response because artifacts that arise at the edges of the modules degrade spatial resolution and sensitivity. Some improvements that may be achieved via the disclosed embodiments are: large field of view (FOV), allowing continuous scanning of an entire target object or body (e.g., whole mouse scanning); high spatial resolution (approximately 0.5 mm) that is homogeneous across the entire FOV; high sensitivity (e.g., at least twice that of the Bruker Albira Si); timing (1.5 ns FWHM) and energy resolution that is better than the Albira-Si PET scanner (e.g., by approximately 15-18%).

The substantially continuous crystal scintillator 78 may be formed from any suitable material. For example, the crystal 78 may include, but is not limited to, LYSO (Cerium-doped Lutetium Yttrium Orthosilicate), $LaBr_3$ (Lanthanum Bromide), NaI(Tl) (Sodium Iodide), BGO (Bismuth Germanate), a combination thereof, or any other suitable scintillator material. The scintillator including the substantially continuous crystal scintillator 78 may be a dense material capable of converting a highly energy gamma ray (e.g., 511 keV in the case of positron emitters), and lower energy in the case of single gamma emitters, such as, but not limited to, $^{99m}Tc$, and $^{111}In$) into visible light. The visible light may be detected by one or more photodetectors 80. The one or more photodetectors 80, may include, but are not limited to, avalanche photo diodes, silicon photomultipliers (SiPMs), or any other suitable photodetector.

In the PET system 72, the PET assembly 50 is under control of the detector acquisition circuitry 56, as described above. Further, the image processing circuitry 58 is communicatively coupled to the detector acquisition circuitry 56 to receive and process the PET image data, as described in detail above. Likewise, the operator workstation 68 may be included in the PET system 72 to enable operator input. Additionally, an output device 82, such as a display or printer, may be configured to output the PET images generated during operation of the PET imaging system 72.

Figure 3:
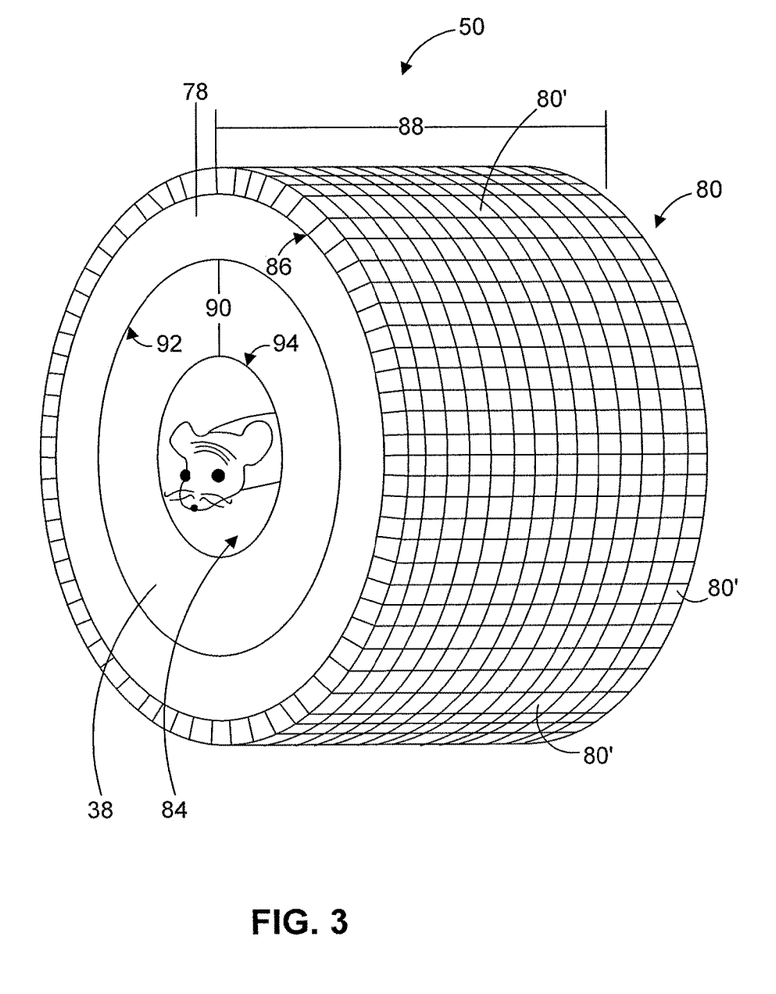
FIG. 3 is a perspective view of an embodiment of a PET assembly disposed about an RF coil.

FIG. 3 illustrates a perspective view of one embodiment of the PET assembly 50. In this embodiment, the PET assembly 50 is formed as an annular (e.g., tube), substantially continuous crystal scintillator 78. In this embodiment, the annular crystal 78 forms a bore 84 extending therethrough. In the illustrated embodiment, the PET assembly 50 is shown disposed about the RF coil 38, which is received in the bore 84. In this way, the PET assembly 50 may be provided as a removable insert that may be inserted around an existing RF coil 38 in an MRI system and removed from the MRI system if desired.

Additionally, in this embodiment, the photodetectors 80 include a plurality of photodetectors 80' disposed on an annular shaped printed circuit board 86 adjacent to the annular scintillator crystal 78. In this embodiment, the photodetectors 80' are curved to match the annular profile of the scintillator crystal 78. The photodetectors 80' may also be disposed in a matrix having multiple rows and columns, as depicted, or as a single row of photodetectors 80' disposed annularly around the crystal 78.

In the illustrated PET assembly 50, the photodetectors 80 and the crystal 78 a uniform length 88. However, in other embodiments, the length 88 of the photodetectors 80 may be different than a length of the crystal 78, as discussed in more detail below. Further, the crystal 78 has a wall thickness 90 between an outer wall 92 and an inner wall 94.

Figure 4:
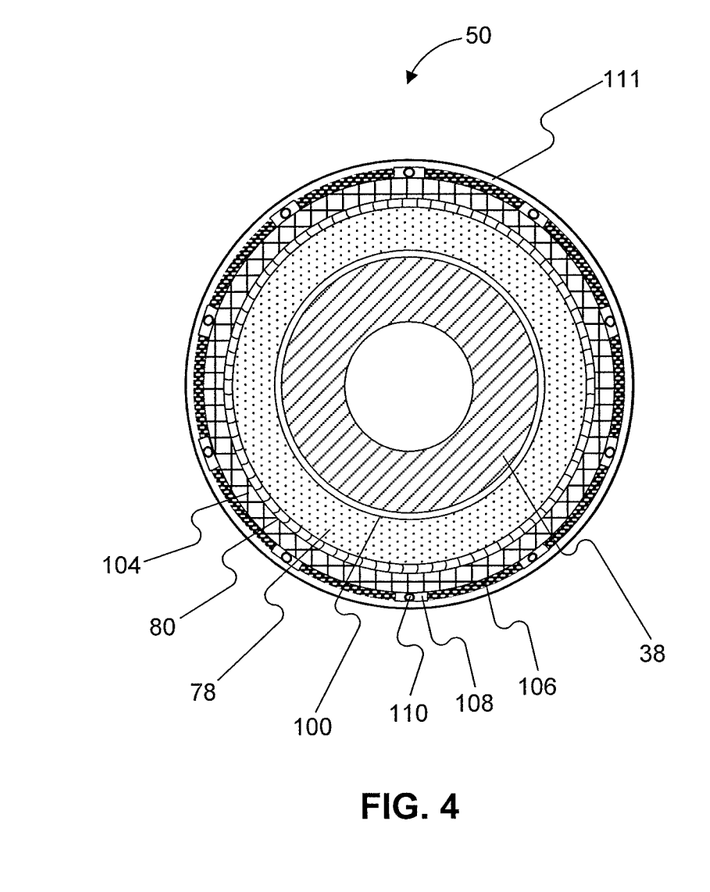
FIG. 4 is a cross-sectional view of an embodiment of a PET assembly having an annular continuous crystal scintillator tube.
Figure 5:
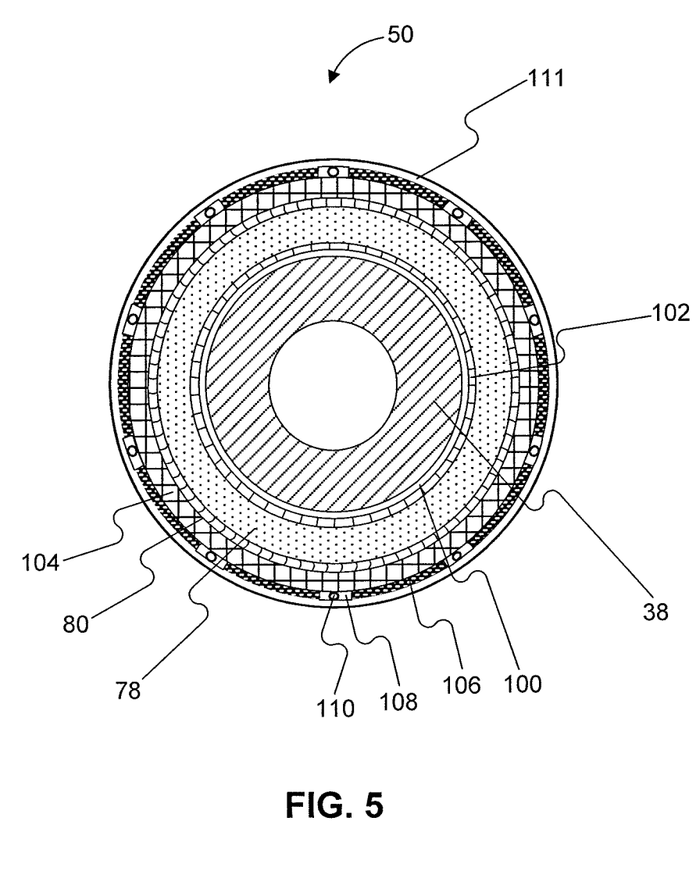
FIG. 5 is a cross-sectional view of another embodiment of the PET assembly having an annular continuous crystal scintillator tube embedded between two rings of photodetectors.

FIGS. 4 and 5 each depict cross-sectional views of embodiments of the PET assembly 50. In the illustrated embodiments, the PET assembly 50 is shown disposed about the RF coil 38 for illustrative purposes only. Indeed, the PET assembly 50 may be provided without the RF coil 38, in a cylindrical bore of an imaging device not having an RF coil, etc.

The PET assembly 50 may include an outer, annular housing 111 configured to enclose one or more components of the PET assembly 50. In the illustrated embodiment, the housing 111 encloses a printed circuit board (PCB) 106. The PCB 106 may be annular to match the curved surface of the crystal 78. Further, in some embodiments, the PCB 106 may be a similar setup that is compatible with the curved surface of the scintillator tube 78. In the illustrated embodiment, the PCB 106 includes a plurality of channels 108 with a plurality of fluid tubes 110 disposed therein at a plurality of radial locations about the circumference of the PCB 106. During operation, the control circuitry 60 may control the fluid source 64 to circulate a cooling fluid through the fluid tubes 110 at a temperature less than a temperature of the PCB 106 to cool the PCB 106.

The PCB 106 may enclose an electronics volume 104, which schematically represents the area provided for the electronics of the PCB 106. The photodetectors 80 are disposed within the electronics volume 104 and are annularly adjacent to the annular, substantially continuous scintillator crystal 78. An annular support 100, such as, but not limited to, a carbon fiber support, provides a frame or housing to complete the PET assembly 50. That is, the housing 111 and the support 100 enclose the components of the PET assembly 50.

In the embodiment of FIG. 5, a second set of one or more photodetectors 102 is annularly disposed between the support 100 and the scintillator crystal 78. In some embodiments, by disposing photodetectors 80, 102 on both the inner surface 94 (shown in FIG. 3) and the outer surface 92

(shown in FIG. 3) of the crystal 78, the shape of the light created by the gamma rays may be better visualized, as compared to implementations including only photodetectors 80. The foregoing feature may enable detection of the depth inside the scintillator crystal 78 and the direction from which the high-energy gamma originated. This may enable improved PET images to be generated because of better ability to determine the line of response along which the positron annihilation occurred.

Figure 6:
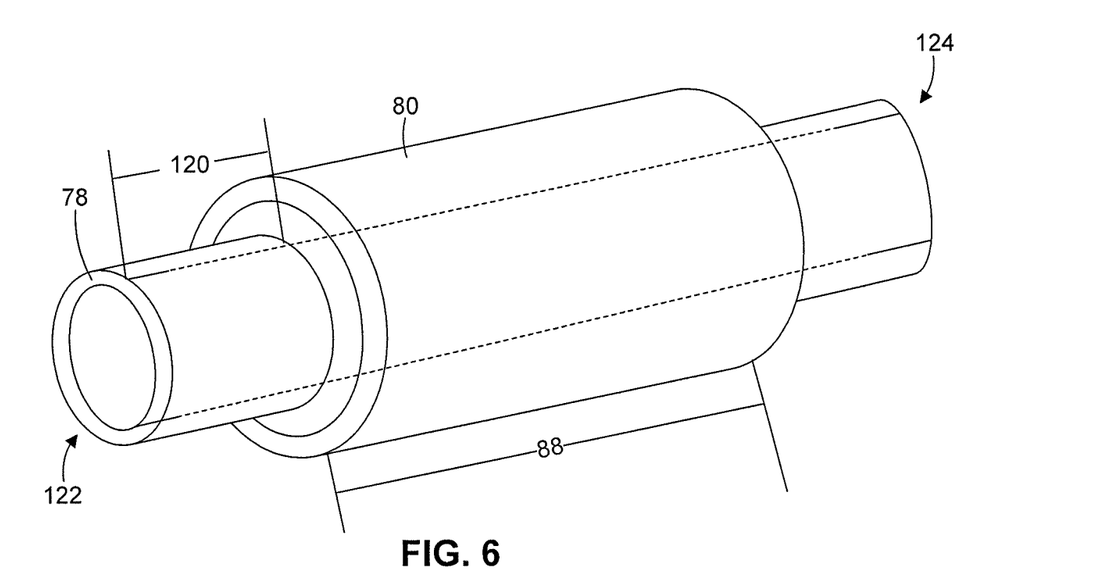
FIG. 6 is a schematic illustration of an embodiment of the arrangement between an annular scintillator crystal and an annular plurality of photodetectors.

FIG. 6 is a schematic illustration of one embodiment of the relative configuration between the annular, substantially continuous crystal scintillator tube 78 and the photodetectors 80. In this embodiment, the annular crystal 78 may extend beyond the length 88 of the photodetectors 80 by a distance 120 on each of a first end 122 and a second end 124 of the PET assembly 50. In one embodiment, the distance 120 on each end may be approximately equal to the thickness 90 of the wall of the crystal 78. This embodiment may be advantageous in certain implementations to reduce or eliminate the quantity of crystal edges present in the portion of the crystal 78 adjacent the photodetectors 80.

Figure 7:
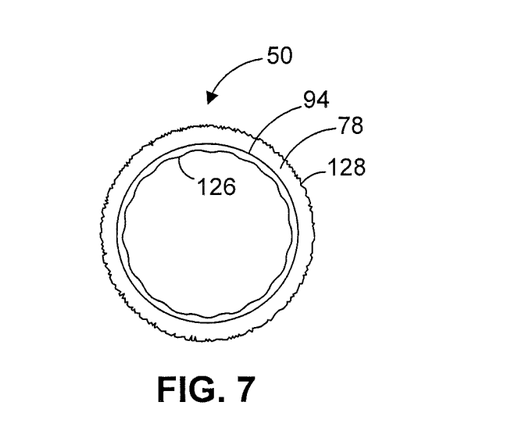
FIG. 7 is a schematic illustration of an embodiment of a crystal scintillator having a coated surface and an etched surface.

FIG. 7 is a schematic illustration of a cross-section of one embodiment of the PET assembly 50. In this embodiment, the inner surface 94 of the crystal 78 includes a light absorbent coating 126. In some embodiments, the light absorbent coating 126 may include a light absorbing material, such as black paint. However, in other embodiments, the coating 126 may be any coating that absorbs light at a desired wavelength. The light absorbent coating 126 will increase the likelihood that light is absorbed proximate the inner surface 94 of the crystal. By doing so, the light may be contained to reduce or prevent the likelihood that the scintillation light will cascade through the volume of the crystal 78. More specifically, the coating 126 may reduce or prevent the likelihood of scintillation light reflecting throughout the entire crystal 78, thus preventing accurate light detection.

Further, in the illustrated embodiment, an etched surface 128 (e.g., roughened) is provided on the outer wall of the crystal 78. Like the light absorbent coating 126, the etched surface 128 increases the likelihood that the light will exit the crystal 78 and increase the amount of light reaching the photomultipliers. The etched surface also will reduce the likelihood that the scintillation light will reflect back into the crystal 78. However, it should be noted that the etched surface 128 and the coating 126 are merely examples. In order to minimize light reflecting within the crystal 78, a variety of suitable methods may be used. For example, the inner surface of the crystal 78 and/or the ends 122 and 124 of the crystal may be treated with the light absorbent coating 126. For further example, the exit surface of the crystal 78 may be joined to the photodetectors 80 with a binding agent that matches the refractive index of the crystal 78. In some embodiments, a mechanically roughed surface may transmit up to approximately 25% more light than a smooth surface, and may improve spatial and timing resolution by approximately 15%.

In other embodiments, only one of the coating 126 and the etched surface 128 may be employed, the etched surface may be on the inner wall 94, the coating 126 may be provided in place of the etched surface 128, etc. For further example, the inner and outer surfaces of the crystal 78 may be processed (e.g., polished) in any suitable manner to reduce light reflections, not limited to those disclosed herein. Indeed, any combination or implementation of the light containment devices provided herein may be employed, depending on implementation-specific considerations.

The embodiments of the PET assembly 50 and imaging systems described herein may have one or more advantages over conventional systems. For example, in embodiments using a single crystal 78 that is continuous, mechanical and optical gaps may be reduced or eliminated, thereby maximizing spatial resolution, sensitivity, and uniformity of response. The sampling of the light distribution may be more uniform (e.g., substantially flat and homogeneous), particularly when compared at the edges of current detector modules.

Further, the substantially continuous crystal scintillator tube 78 may enable the tails of light distributions to not be truncated, making it possible to measure depth of interaction (DOI) more accurately. Additionally, because of the large field of view enabled by embodiments of the PET assembly 50, dynamic, multi-organ imaging may be enabled. Further, the mechanical simplicity of certain embodiments of the PET assembly 50 (e.g., where there is only one scintillator crystal 78 and one SiPM array (readout sampled)) may render the PET assembly 50 easier and less expensive to build than multi-crystal scanners.

It should be noted that the products and/or processes disclosed may be used in combination or separately. Additionally, exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the prior detailed description be considered as exemplary only, with the true scope and spirit being indicated by the following claims.

The examples presented herein are for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

What is claimed is:

1. An imaging device, comprising:
   an annular housing of a positron emission tomography (PET) assembly;
   an annular scintillator disposed within the annular housing, the annular scintillator comprising a curved, annular, and continuous crystal configured to absorb ionizing radiation and to emit light energy, wherein the annular scintillator is configured to detect two photons emitted from a positron-electron annihilation, wherein the annular scintillator includes multiple elements joined together to form a pseudo single crystal tube configured to propagate light through edges of the multiple elements without refracting the light; and a plurality of photodetectors annularly disposed around the annular scintillator within the annular housing and configured to detect the emitted light energy;

wherein the plurality of photodetectors are disposed on an annular printed circuit board, and wherein the multiple elements, the plurality of photodetectors, and the annular printed circuit board are curved to match an annular profile of the annular scintillator.

2. The imaging device of claim 1, wherein the photodetectors comprise a plurality of photomultipliers, and a length of the annular scintillator is longer than the coverage of the photomultipliers, and a first end of the annular scintillator extends beyond a first end of the photomultipliers, while a second end of the annular scintillator extends beyond a second end of the photomultipliers.

3. The imaging device of claim 1, wherein each of the plurality of photodetectors comprises a silicon photomultiplier (SiPM).

4. The imaging device of claim 1, wherein the pseudo single crystal tube includes LYSO (Cerium-doped Lutetium Yttrium Orthosilicate).

5. The imaging device of claim 1, wherein a light-absorbing material is disposed on an inner surface of the annular scintillator.

6. The imaging device of claim 5, wherein an outer surface of the annular scintillator is etched.

7. The imaging device of claim 1, wherein the multiple elements comprise a plurality of crystals joined together via optical matching glue disposed between each of the plurality of crystals, wherein a refractive index of each of the plurality of crystals is approximately equal to a refractive index of the optical matching glue.

8. An imaging device, comprising:
an annular housing of a positron emission tomography (PET) assembly;
an annular scintillator disposed within the annular housing and comprising an annular pseudo single crystal tube configured to absorb ionizing radiation and to emit light energy, wherein the annular scintillator is configured to detect two photons emitted from a positron-electron annihilation, and wherein the pseudo single crystal tube includes multiple crystals joined together such that the refractive index throughout the volume of the annular scintillator is approximately equal; and
a plurality of photodetectors annularly disposed around the annular scintillator within the annular housing and configured to detect the emitted light energy;
wherein the plurality of photodetectors are disposed on an annular printed circuit board, and
wherein the multiple crystals, the plurality of photodetectors, and the annular printed circuit board are curved to match an annular profile of the annular scintillator.

9. The imaging device of claim 8, wherein the multiple crystals are joined together with optical matching glue.

10. The imaging device of claim 9, wherein the optical matching glue has a refractive index approximately equal to the refractive index of the multiple crystals.

11. The imaging device of claim 8, wherein the pseudo single crystal tube is not pixelated.

12. The imaging device of claim 8, wherein the pseudo single crystal tube includes LYSO (Cerium-doped Lutetium Yttrium Orthosilicate).

13. The imaging device of claim 8, wherein a light-absorbing material is disposed on an inner surface of the annular scintillator.

14. The imaging device of claim 13, wherein an outer surface of the annular scintillator is etched.

15. An imaging device, comprising:
an annular housing of a positron emission tomography (PET) assembly;
an annular scintillator disposed within the annular housing and comprising curved, annular, and substantially continuous crystal configured to absorb ionizing radiation and to emit light energy, wherein the annular scintillator is configured to detect two photons emitted from a positron-electron annihilation, wherein the annular, substantially continuous crystal comprises a plurality of crystals and optical matching glue disposed between each of the plurality of crystals, and wherein a refractive index of each of the plurality of crystals is approximately equal to a refractive index of the optical matching glue;
a plurality of photodetectors annularly disposed around the annular scintillator within the annular housing and configured to detect the emitted light energy;
wherein the plurality of photodetectors are disposed on an annular printed circuit board, and
wherein the plurality of crystals, the plurality of photodetectors, and the annular printed circuit board are curved to match an annular profile of the annular scintillator.

16. The imaging device of claim 15, wherein a light-absorbing material is disposed on an inner surface of the annular scintillator.

17. The imaging device of claim 16, wherein an outer surface of the annular scintillator is etched.

18. The imaging device of claim 15, wherein each of the plurality of photodetectors comprises a silicon photomultiplier (SiPM).

* * * * *

UNITED STATES PATENT AND TRADEMARK OFFICE
CERTIFICATE OF CORRECTION

PATENT NO. : 11,213,264 B2
APPLICATION NO. : 15/778053
DATED : January 4, 2022
INVENTOR(S) : Stuart S. Berr et al.

It is certified that error appears in the above-identified patent and that said Letters Patent is hereby corrected as shown below:

On the Title Page

Inventors, Line 3, "JosE Maria" should read as --José María--.

Signed and Sealed this
Eighteenth Day of October, 2022

Katherine Kelly Vidal
*Director of the United States Patent and Trademark Office*